US008889110B2

(12) United States Patent
Braida-Valerio et al.

(10) Patent No.: US 8,889,110 B2
(45) Date of Patent: Nov. 18, 2014

(54) OXIDIZING COMPOSITION FOR THE TREATMENT OF KERATIN FIBERS COMPRISING AT LEAST ONE OIL, AT LEAST ONE FATTY ALCOHOL AND AT LEAST ONE OXYALKYLENATED FATTY ALCOHOL

(75) Inventors: Damarys Braida-Valerio, Paris (FR); Frédéric Simonet, Clichy (FR); Luc Nicolas-Morgantini, Rully (FR)

(73) Assignee: L'OREAL, Paris (FR)

( * ) Notice: Subject to any disclaimer, the term of this patent is extended or adjusted under 35 U.S.C. 154(b) by 743 days.

(21) Appl. No.: 12/642,568

(22) Filed: Dec. 18, 2009

(65) Prior Publication Data

US 2010/0158844 A1 Jun. 24, 2010

Related U.S. Application Data

(60) Provisional application No. 61/144,212, filed on Jan. 13, 2009.

(30) Foreign Application Priority Data

Dec. 19, 2008 (FR) .................................. 08 58840

(51) Int. Cl.
| | | |
|---|---|---|
| A61K 8/00 | (2006.01) | |
| A61K 8/18 | (2006.01) | |
| A61Q 5/00 | (2006.01) | |
| A61Q 9/00 | (2006.01) | |
| A61Q 5/04 | (2006.01) | |
| A61K 8/31 | (2006.01) | |
| A61K 8/22 | (2006.01) | |
| A61K 8/39 | (2006.01) | |
| A61Q 5/08 | (2006.01) | |
| A61Q 5/10 | (2006.01) | |
| A61K 8/86 | (2006.01) | |
| A61K 8/37 | (2006.01) | |
| A61K 8/34 | (2006.01) | |

(52) U.S. Cl.
CPC ... *A61K 8/22* (2013.01); *A61Q 5/04* (2013.01); *A61K 8/31* (2013.01); *A61K 8/39* (2013.01); *A61Q 5/08* (2013.01); *A61Q 5/10* (2013.01); *A61K 8/86* (2013.01); *A61K 8/375* (2013.01); *A61K 8/342* (2013.01)
USPC ......................................................... 424/70.1

(58) Field of Classification Search
USPC ........................................................ 424/70.1
See application file for complete search history.

(56) References Cited

U.S. PATENT DOCUMENTS

| | | | |
|---|---|---|---|
| 3,100,739 A | 8/1963 | Kaiser et al. | |
| 3,369,970 A | 2/1968 | McLaughlin et al. | |
| 3,629,330 A | 12/1971 | Brody et al. | |
| 3,861,868 A | 1/1975 | Milbrada | |
| 4,138,478 A | 2/1979 | Reese et al. | |
| 4,169,704 A * | 10/1979 | Fakhouri | 8/421 |
| 4,170,637 A | 10/1979 | Pum | |
| 4,226,851 A | 10/1980 | Sompayrac | |
| 4,357,141 A | 11/1982 | Grollier et al. | |
| 4,366,099 A | 12/1982 | Gaetani et al. | |
| 4,488,564 A | 12/1984 | Grollier et al. | |
| 4,725,282 A | 2/1988 | Hoch et al. | |
| 4,826,681 A | 5/1989 | Jacquet et al. | |
| 4,845,293 A | 7/1989 | Junino et al. | |
| 5,021,066 A | 6/1991 | Aeby et al. | |
| 5,259,849 A | 11/1993 | Grollier et al. | |

(Continued)

FOREIGN PATENT DOCUMENTS

| | | |
|---|---|---|
| CA | 1 268 421 | 5/1990 |
| CA | 2 573 567 | 3/2006 |

(Continued)

OTHER PUBLICATIONS

French Search Report for FR 08/58840, dated Sep. 30, 2009.
English language Abstract of DE 10 2005 011 459, dated Sep. 14, 2006.
English language Abstract of EP 2 005 939, dated Dec. 24, 2008.
Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.
Copending U.S. Appl. No. 12/642,412, filed Dec. 18, 2009.
Copending U.S. Appl. No. 12/642,451, filed Dec. 18, 2009.
Copending U.S. Appl. No. 12/642,468, filed Dec. 18, 2009.

(Continued)

*Primary Examiner* — Trevor Love
(74) *Attorney, Agent, or Firm* — The Marbury Law Group, PLLC

(57) ABSTRACT

Provided herein is a composition for the treatment of keratin fibers comprising, a cosmetically acceptable medium; at least one fatty alcohol; at least one oxyalkylenated fatty alcohol; at least one oxidizing agent; and at least one oil other than a fatty alcohol present in an amount greater than or equal to 10% by weight relative to the total weight of the composition, wherein the weight ratio of the at least one fatty alcohol to the at least one oxyalkylenated fatty alcohol has a value less than or equal to 5; and further wherein the pH of the composition ranges from 1.5 to 4.5. Also provided herein is a composition for the treatment of keratin fibers comprising, a cosmetically acceptable medium; at least one fatty alcohol present in an amount ranging from 3 to 25% by weight relative to the total weight of the composition; at least one oxyalkylenated fatty alcohol; at least one oxidizing agent; and at least one oil other than a fatty alcohol present in an amount greater than or equal to 10% by weight relative to the total weight of the composition, wherein the weight ratio of the at least one fatty alcohol to the at least one oxyalkylenated fatty alcohol has a value less than or equal to 5; and further wherein the pH of the composition is alkaline. Also provided herein is a method for treating keratin fibers, comprising applying to the keratin fibers at least one oxidizing composition described herein.

14 Claims, No Drawings

(56) References Cited

U.S. PATENT DOCUMENTS

| | | |
|---|---|---|
| 5,364,414 A | 11/1994 | Lang et al. |
| 5,817,155 A | 10/1998 | Yasuda et al. |
| 6,010,541 A | 1/2000 | De La Mettrie et al. |
| 6,074,439 A | 6/2000 | De La Mettrie et al. |
| 6,129,770 A | 10/2000 | Deutz et al. |
| 6,156,713 A | 12/2000 | Chopra et al. |
| 6,165,444 A | 12/2000 | Dubief et al. |
| 6,190,421 B1 | 2/2001 | Rondeau et al. |
| 6,206,935 B1 | 3/2001 | Onitsuka et al. |
| 6,238,653 B1 | 5/2001 | Narasimhan et al. |
| 6,251,378 B1 | 6/2001 | Laurent et al. |
| 6,260,556 B1 | 7/2001 | Legrand et al. |
| 6,277,154 B1 | 8/2001 | Lorenz |
| 6,277,155 B1 | 8/2001 | De La Mettrie et al. |
| 6,365,136 B1 | 4/2002 | Lauscher et al. |
| 6,423,100 B1 | 7/2002 | Lang et al. |
| 6,447,552 B1 | 9/2002 | Golinski |
| 6,645,258 B2 | 11/2003 | Vidal et al. |
| 6,660,045 B1 | 12/2003 | Hoeffkes et al. |
| 6,695,887 B2 | 2/2004 | Cottard et al. |
| 6,800,098 B1 | 10/2004 | Allard et al. |
| 7,135,046 B2 | 11/2006 | Audousset |
| 7,153,331 B2 | 12/2006 | Desenne et al. |
| 7,217,298 B2 | 5/2007 | Legrand et al. |
| 7,285,137 B2 | 10/2007 | Vidal et al. |
| 7,442,215 B2 | 10/2008 | Audousset et al. |
| 7,458,993 B2 | 12/2008 | Cottard et al. |
| 7,494,513 B2 | 2/2009 | Kravtchenko et al. |
| 7,575,605 B2 | 8/2009 | Legrand |
| 7,651,533 B2 | 1/2010 | Legrand |
| 7,651,536 B2 | 1/2010 | Cottard et al. |
| 7,740,663 B2 | 6/2010 | De La Mettrie et al. |
| 7,766,977 B2 | 8/2010 | Cottard et al. |
| 7,799,095 B2 | 9/2010 | Mario et al. |
| 2003/0190297 A1 | 10/2003 | Narasimham et al. |
| 2003/0226217 A1 | 12/2003 | Bowes et al. |
| 2004/0103488 A1 | 6/2004 | Yamashita et al. |
| 2004/0105830 A1 | 6/2004 | Boswell et al. |
| 2004/0181883 A1 | 9/2004 | Legrand et al. |
| 2004/0226110 A1 | 11/2004 | LeGrand |
| 2004/0235700 A1 | 11/2004 | Legrand et al. |
| 2005/0129652 A1 | 6/2005 | Keller et al. |
| 2005/0165705 A1 | 7/2005 | Lauper et al. |
| 2005/0196367 A1 | 9/2005 | Ohta et al. |
| 2006/0042023 A1 | 3/2006 | Machida |
| 2006/0075580 A1 | 4/2006 | Chan et al. |
| 2006/0137111 A1 | 6/2006 | Au et al. |
| 2006/0242773 A1 | 11/2006 | Kravtchenko et al. |
| 2006/0260071 A1 | 11/2006 | Legrand |
| 2006/0265817 A1 | 11/2006 | Legrand |
| 2007/0006397 A1 | 1/2007 | Schmenger et al. |
| 2007/0033743 A1 | 2/2007 | Kravtchenko |
| 2007/0104672 A1 | 5/2007 | Decoster et al. |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1 | 1/2008 | Cottard et al. |
| 2008/0071092 A1 | 3/2008 | Vidal et al. |
| 2008/0229512 A1 | 9/2008 | Syed et al. |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1 | 6/2009 | Brun |
| 2009/0151087 A1 | 6/2009 | Mario et al. |
| 2009/0158533 A1 | 6/2009 | Hercouet |
| 2009/0162309 A1 | 6/2009 | Hercouet et al. |
| 2009/0191142 A1 | 7/2009 | Hercouet et al. |

FOREIGN PATENT DOCUMENTS

| | | |
|---|---|---|
| CH | 507 713 | 7/1971 |
| DE | 20 05 076 | 8/1970 |
| DE | 38 14 356 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |
| DE | 197 54 281 | 6/1999 |
| DE | 198 15 338 | 9/1999 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 193 471 | 9/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 | 1/2004 |
| EP | 1 430 873 | 6/2004 |
| EP | 1 438 951 | 7/2004 |
| EP | 1 449 512 | 8/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 | 11/2005 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 473 | 1/2009 |
| EP | 2 011 474 | 1/2009 |
| EP | 2 018 848 | 1/2009 |
| EP | 2 072 034 | 6/2009 |
| EP | 2 072 035 | 6/2009 |
| EP | 2 072 036 | 6/2009 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 | 6/2007 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |

(56) References Cited

FOREIGN PATENT DOCUMENTS

| | | |
|---|---|---|
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| GB | 1 288 128 | 9/1972 |
| GB | 2 003 938 | 3/1979 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-81792 | 3/2003 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |
| WO | WO 01/28508 | 4/2001 |
| WO | WO 01/41723 | 6/2001 |
| WO | WO 01/43709 | 6/2001 |
| WO | WO 01/60327 | 8/2001 |
| WO | WO 02/089748 | 11/2002 |
| WO | WO 03/053329 | 7/2003 |
| WO | WO 03/084495 | 10/2003 |
| WO | WO 2005/025525 | 3/2005 |
| WO | WO 2005/055966 | 6/2005 |
| WO | WO 2006/026851 | 3/2006 |
| WO | WO 2007/006418 | 1/2007 |
| WO | WO 2007/096027 | 8/2007 |
| WO | WO 2008/021641 | 2/2008 |
| WO | WO 2008/096497 | 8/2008 |
| WO | WO 2008/138844 | 11/2008 |
| WO | WO 2009/010883 | 1/2009 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

Copending U.S. Appl. No. 12/642,473, filed Dec. 18, 2009.
Copending U.S. Appl. No. 12/642,480, filed Dec. 18, 2009.
Copending U.S. Appl. No. 12/642,489, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.
Copending U.S. Appl. No. 12/642,531, filed Dec. 18, 2009.
Copending U.S. Appl. No. 12/642,536, filed Dec. 18, 2009.
Copending U.S. Appl. No. 12/642,543, filed Dec. 18, 2009.
Copending U.S. Appl. No. 12/642,551, filed Dec. 18, 2009.
Copending U.S. Appl. No. 12/642,555, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
Copending U.S. Appl. No. 12/976,093, filed Dec. 22, 2010.
Copending U.S. Appl. No. 12/976,124, filed Dec. 22, 2010.

English language Abstract of DE 10 2005 032 798, dated Jan. 25, 2007.
English language Abstract of DE 10 2005 059 647, dated Jun. 14, 2007.
English language Abstract of DE 10 2006 012 575, dated Feb. 8, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of DE 199 62 869, dated Jun. 28, 2001.
English language Abstract of DE 38 14 356, dated Sep. 8, 1988.
English language Abstract of DE 43 09 509, dated Sep. 19, 1994.
English language Abstract of EP 1 166 749, dated Jan. 22, 2002.
English language Abstract of EP 1 321 132, dated Jun. 25, 2003.
English language Abstract of EP 1 568 354, dated Aug. 31, 2005.
English language Abstract of EP 1 862 198, dated Dec. 5, 2007.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 304, dated Jun. 26, 2009.
English language Abstract of FR 2 925 308, dated Jun. 26, 2009.
English language Abstract of FR 2 925 309, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/006418, dated Jan. 18, 2007.
English language Abstract of WO 2007/096027, dated Aug. 30, 2007.
English language Abstract of WO 2008/096497, dated Aug. 14, 2008.
English language Abstract of WO 91/11985, dated Aug. 22, 1991.
English language Abstract of WO 97/04739, dated Feb. 13, 1997.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
European Search Report for EP 10 15 5935, dated Oct. 8, 2010.
French Search Report for FR 07/60273, dated Aug. 20, 2008.
French Search Report for FR 07/60274, dated Aug. 20, 2008.

(56) References Cited

OTHER PUBLICATIONS

French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.
French Search Report for FR 08/07306, dated Aug. 13, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58880, dated Sep. 18, 2009.
French Search Report for FR 08/58881, dated Sep. 29, 2009.
French Search Report for FR 08/58886, dated Nov. 3, 2009.
French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.
French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.
French Search Report for FR 09/59388, dated Aug. 3, 2010.
French Search Report for FR 09/59391, dated Sep. 16, 2010.
International Search Report for PCT/FR2009/052617, dated Mar. 30, 2010.
Notice of Allowance mailed Aug. 10, 2010, in U.S. Appl. No. 12/339,820.
Notice of Allowance mailed Aug. 26, 2010, in U.S. Appl. No. 12/642,624.
Notice of Allowance mailed Aug. 26, 2010, in U.S. Appl. No. 12/642,637.
Notice of Allowance mailed Aug. 27, 2010, in U.S. Appl. No. 12/642,513.
Notice of Allowance mailed Dec. 10, 2010, in U.S. Appl. No. 12/642,599.
Notice of Allowance mailed Dec. 14, 2010, in U.S. Appl. No. 12/642,551.
Notice of Allowance mailed Dec. 15, 2010, in U.S. Appl. No. 12/642,637.
Notice of Allowance mailed Dec. 20, 2010, in U.S. Appl. No. 12/642,531.
Notice of Allowance mailed Dec. 20, 2010, in U.S. Appl. No. 12/642,575.
Notice of Allowance mailed Dec. 28, 2010, in U.S. Appl. No. 12/642,536.
Notice of Allowance mailed Dec. 29, 2010, in U.S. Appl. No. 12/642,480.
Notice of Allowance mailed Dec. 29, 2010, in U.S. Appl. No. 12/642,555.
Notice of Allowance mailed Dec. 8, 2010, in U.S. Appl No. 12/642,473.
Notice of Allowance mailed in co-pending U.S. Appl. No. 12/339,753, dated Jul. 9, 2010.
Notice of Allowance mailed Jan. 28, 2011, in U.S. Appl. No. 12/642,592.
Notice of Allowance mailed Jun. 11, 2010, in U.S. Appl. No. 12/642,489.
Notice of Allowance mailed Nov. 19, 2010, in U.S. Appl. No. 12/339,820.
Notice of Allowance mailed Nov. 26, 2010, in U.S. Appl. No. 12/642,513.
Notice of Allowance mailed Nov. 26, 2010, in U.S. Appl. No. 12/642,543.
Notice of Allowance mailed Nov. 30, 2010, in U.S. Appl. No. 12/642,624.
Notice of Allowance mailed Oct. 26, 2010, in U.S. Appl. No. 12/339,753.
Notice of Allowance mailed Sep. 16, 2010, in U.S. Appl. No. 12/642,480.
Notice of Allowance mailed Sep. 16, 2010, in U.S. Appl. No. 12/642,555.
Notice of Allowance mailed Sep. 21, 2010, in U.S. Appl. No. 12/642,489.
Notice of Allowance mailed Sep. 22, 2010, in U.S. Appl. No. 12/642,551.
Notice of Allowance mailed Sep. 23, 2010, in U.S. Appl. No. 12/642,536.
Notice of Allowance mailed Sep. 7, 2010, in U.S. Appl. No. 12/642,599.
Notice of Allowance mailed Sep. 8, 2010, in U.S. Appl. No. 12/642,543.
Notice of Allowance mailed Sep. 9, 2010, in U.S. Appl. No. 12/642,531.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Dec. 17, 2010, in co-pending U.S. Appl. No. 12/642,451.
Office Action mailed Feb. 1, 2010, in co-pending U.S. Appl. No. 12/339,753.
Office Action mailed Mar. 15, 2010, in co-pending U.S. Appl. No. 12/339,820.
Office Action mailed Nov. 22, 2010, in co-pending U.S. Appl. No. 12/642,593.
Office Action mailed Sep. 17, 2010, in co-pending U.S. Appl. No. 12/642,506.
Office Action mailed Sep. 21, 2010, in co-pending U.S. Appl. No. 12/642,468.
Office Action mailed Sep. 22, 2010, in co-pending U.S. Appl. No. 12/642,492.
Office Action mailed Sep. 3, 2010, in co-pending U.S. Appl. No. 12/642,451.
STIC Search Report for U.S. Appl. No. 12/339,820, dated Jan. 21, 2010.
STIC Search Report for U.S. Appl. No. 12/642,492, dated Jul. 14, 2010.
European Search Report for EP 09 17 9779, dated May 5, 2010.
English translation of JP 2003-81792 (14 pages) 2003.
Brown, "Hair and Hair Care," Cosmetic Science and Technology Series, vol. 17, chapter 7, pp. 191-215 1997.

\* cited by examiner

OXIDIZING COMPOSITION FOR THE TREATMENT OF KERATIN FIBERS COMPRISING AT LEAST ONE OIL, AT LEAST ONE FATTY ALCOHOL AND AT LEAST ONE OXYALKYLENATED FATTY ALCOHOL

This application claims benefit of U.S. Provisional Application No. 61/144,212, filed Jan. 13, 2009. This application also claims benefit of priority under 35 U.S.C. §119 to French Patent Application No. 0858840, filed Dec. 19, 2008.

Provided herein is a composition for the treatment of keratin fibers, for example human keratin fibers such as the hair, comprising, in a cosmetically acceptable medium, at least one fatty alcohol; at least one oxyalkylenated fatty alcohol; at least one oxidizing agent; and at least one oil other than a fatty alcohol present in an amount greater than or equal to 10% by weight relative to the total weight of the composition; wherein the weight ratio of the at least one fatty alcohol to the at least one oxyalkylenated fatty alcohol has a value less than or equal to 5.

In cosmetics, in the areas of dyeing and bleaching of keratin fibers, for example human keratin fibers such as the hair, oxidizing compositions are often used.

Thus, in oxidation dyeing of the hair, oxidizing compositions may be mixed with oxidation dyes (bases and couplers), which may be colorless in themselves, to produce colored and coloring compounds by a process of oxidative condensation. Oxidizing compositions may also be used in direct dyeing of the hair mixed with certain direct dyes which are colored and coloring, to obtain coloration with a hair lightening effect. The oxidizing agents used conventionally for the dyeing of keratin fibers include for example hydrogen peroxide or compounds that can produce hydrogen peroxide by hydrolysis, such as urea peroxide. Persalts such as perborates and persulphates can also be used. Hydrogen peroxide for example can also be used.

In hair bleaching, the bleaching compositions may contain at least one oxidizing agent. Among these oxidizing agents, those conventionally used are for example hydrogen peroxide or compounds that can produce hydrogen peroxide by hydrolysis, such as urea peroxide or persalts such as perborates, percarbonates, and persulphates. Hydrogen peroxide and persulphates, for example, can also be used.

These compositions can be aqueous compositions containing alkaline agents (amines or ammonia), which are diluted at the moment of use with an aqueous composition of hydrogen peroxide.

These compositions can also be formed from anhydrous products that contain alkaline compounds (amines and alkaline silicates), a peroxidized reagent such as persulphates, perborates, or percarbonates, and ammonium or alkali metals, which are diluted at the moment of use with an aqueous composition of hydrogen peroxide.

In permanent deformation of the hair, first the disulphide bonds —S—S— of the keratin (cystine) can be opened using a composition containing a suitable reducing agent (reduction stage) then, after rinsing the hair thus treated, secondly the disulphide bonds can be reconstituted by applying, on the hair previously put under tension (curlers etc.), an oxidizing composition (oxidation stage, also called fixation) so as finally to give the hair the desired form. This technique thus may make it possible to carry out either waving or straightening of the hair. The new shape imposed on the hair by chemical treatment as described above may be long-lasting and may withstand the action of washing with water or shampoos, in contrast to the conventional techniques of temporary waving, such as a water wave.

The oxidizing compositions used in the fixation stage are generally compositions based on hydrogen peroxide.

The introduction of a large amount of oil, as a replacement for the water, into oxidizing compositions for dyeing, bleaching, or permanently deforming keratin fibers may improve the effectiveness of the active agents. However, the introduction of a large amount of oil into the oxidizing composition may result in a destabilization of the composition, which may undergo phase separation after a few days.

Provided herein is a composition for the treatment of keratin fibers, for example human keratin fibers such as the hair, comprising,
  a cosmetically acceptable medium;
  at least one fatty alcohol;
  at least one oxyalkylenated fatty alcohol;
  at least one oxidizing agent; and
  at least one oil other than a fatty alcohol present in an amount greater than or equal to 10% by weight relative to the total weight of the composition;
  wherein the weight ratio of the at least one fatty alcohol to the at least one oxyalkylenated fatty alcohol has a value less than or equal to 5; and further wherein the pH of the composition ranges from 1.5 to 4.5.

Provided herein is also a composition for the treatment of keratin fibers comprising,
  a cosmetically acceptable medium;
  at least one fatty alcohol present in an amount ranging from 3 to 25% by weight relative to the total weight of the composition;
  at least one oxyalkylenated fatty alcohol;
  at least one oxidizing agent; and
  at least one oil other than a fatty alcohol present in an amount greater than or equal to 10% by weight relative to the total weight of the composition;
  wherein the weight ratio of the at least one fatty alcohol to the at least one oxyalkylenated fatty alcohol has a value less than or equal to 5; and further wherein the pH of the composition is alkaline.

Provided herein is a method for treating keratin fibers comprising applying to the keratin fibers at least one oxidizing composition comprising,
  a cosmetically acceptable medium;
  at least one fatty alcohol;
  at least one oxyalkylenated fatty alcohol;
  at least one oxidizing agent; and
  at least one oil other than a fatty alcohol present in an amount greater than or equal to 10% by weight relative to the total weight of the composition;
  wherein the weight ratio of the at least one fatty alcohol to the at least one oxyalkylenated fatty alcohol has a value less than or equal to 5; and further wherein the pH of the composition ranges from 1.5 to 4.5.

Provided herein is also a method for treating keratin fibers comprising applying to the keratin fibers at least one oxidizing composition comprising,
  a cosmetically acceptable medium;
  at least one fatty alcohol present in an amount ranging from 3 to 25% by weight relative to the total weight of the composition;
  at least one oxyalkylenated fatty alcohol;
  at least one oxidizing agent; and
  at least one oil other than a fatty alcohol present in an amount greater than or equal to 10% by weight relative to the total weight of the composition;

wherein the weight ratio of the at least one fatty alcohol to the at least one oxyalkylenated fatty alcohol has a value less than or equal to 5; and further wherein the pH of the composition is alkaline.

Provided herein is a method for making an oxidizing composition for treating keratin fibers comprising combining,
  a cosmetically acceptable medium;
  at least one fatty alcohol;
  at least one oxyalkylenated fatty alcohol;
  at least one oxidizing agent; and
  at least one oil other than a fatty alcohol present in an amount greater than or equal to 10% by weight relative to the total weight of the composition;
wherein the weight ratio of the at least one fatty alcohol to the at least one oxyalkylenated fatty alcohol has a value less than or equal to 5; further wherein the pH of the composition ranges from 1.5 to 4.5; and wherein the ingredients can be added in any order.

Provided herein is also a method for making an oxidizing composition for treating keratin fibers comprising combining,
  a cosmetically acceptable medium;
  at least one fatty alcohol present in an amount ranging from 3 to 25% by weight relative to the total weight of the composition;
  at least one oxyalkylenated fatty alcohol;
  at least one oxidizing agent; and
  at least one oil other than a fatty alcohol present in an amount greater than or equal to 10% by weight relative to the total weight of the composition;
wherein the weight ratio of the at least one fatty alcohol to the at least one oxyalkylenated fatty alcohol has a value less than or equal to 5; further wherein the pH of the composition is alkaline; and wherein the ingredients can be added in any order.

When the compositions and methods described herein are used for coloring keratin fibers, good dyeing properties may be obtained, for example strong, chromatic coloring, low selectivity, and good resistance to the various aggressive factors to which the hair may be subjected, such as shampoos, light, sweat, and permanent deformation, without affecting the cosmetic properties of the keratin fibers.

When the compositions and methods described herein are used for the bleaching of keratin fibers, they may provide a good lightening effect of the fibers without degrading them and without affecting their cosmetic properties.

When the compositions and methods described herein are used for the permanent deformation of keratin fibers, they may provide satisfactory permanent deformation of the fibers without degrading them and without affecting their cosmetic properties.

Moreover, the composition described herein may have good stability over time, such as in storage at high temperatures, for example, at a temperature of 45° C.

Also provided herein is a method for treating keratin fibers, such as a method for coloring, bleaching, or permanently deforming keratin fibers, employing at least one oxidizing composition described herein.

Also provided herein is a method for making this oxidizing composition for treating keratin fibers.

Hereinafter, unless stated otherwise, the limits of the stated ranges are included.

The at least one fatty alcohol present in the composition described herein can be selected from non-(poly)oxyalkylenated (the alkyl having 1 to 3 carbon atoms) and non(poly) glycerolated alcohols comprising at least one fatty chain having from 10 to 30 carbon atoms, for example from 14 to 22 carbon atoms and for instance from 16 to 18 carbon atoms, said alcohols being saturated or unsaturated, the at least one fatty chain being optionally substituted with one or two additional hydroxyl groups. When the at least one fatty alcohol is unsaturated, it may comprise from 1 to 3 conjugated or non-conjugated carbon-carbon double bonds (—C=C—). The at least one fatty alcohol may be, for example, a monoalcohol.

As examples of fatty alcohols, non-limiting mention may be made of lauryl alcohol, cetyl alcohol, stearyl alcohol, behenyl alcohol, myristyl alcohol, linoleyl alcohol, undecylenyl alcohol, palmitoleyl alcohol, linolenyl alcohol, arachidonyl alcohol, erucyl alcohol, isocetyl alcohol, isostearyl alcohol, isobehenyl alcohol and oleyl alcohol, and mixtures thereof.

In some embodiments, the composition described herein can comprise at least one non(poly)oxyalkylenated and non (poly)glycerolated saturated fatty monoalcohol containing from 14 to 22 carbon atoms, and for example from 16 to 18 carbon atoms.

The composition described herein can have at least one fatty alcohol present in an amount ranging from 3 to 25% by weight relative to the total weight of the composition, for example from 5 to 20% by weight, and for instance from 6 to 18% by weight.

The at least one oxyalkylenated fatty alcohol can be selected from those of formula (I) below:

wherein:
R is a linear or branched, saturated or unsaturated radical containing from 8 to 40 carbon atoms, for example from 8 to 30;
Z represents an oxyethylenated (i) and/or oxypropylenated $(ii)_1$ and $(ii)_2$ radical having the respective formulae below:

and
m represents the number of ethylene oxide (i) and/or propylene oxide $(ii)_1$ or $(ii)_2$ groups, ranging from 1 to 250, for example from 2 to 100.

In some embodiments, the at least one oxyalkylenated fatty alcohol can be a linear or branched, saturated or unsaturated fatty alcohol containing from 10 to 20 carbon atoms and 2 to 40 ethylene oxide groups.

As examples of the at least one oxyalkylenated fatty alcohol, non-limiting mention may be made of the following commercially available products:
  Mergital LM2 (COGNIS) [lauryl alcohol 2 EO];
  Ifralan L12 (IFRACHEM) and Rewopal 12 (GOLDSCHMIDT) [lauryl alcohol 12 EO];
  Empilan KA 2.5/90FL (ALBRIGHT & WILSON) and Mergital BL309 (COGNIS) [decyl alcohol 3 EO];
  Empilan KA 5/90FL (ALBRIGHT & WILSON) and Mergital BL589 (COGNIS) [decyl alcohol 5 EO];

Brij 58 (UNIQEMA) and Simulsol 58 (SEPPIC) [cetyl alcohol 20 EO];

Eumulgin 05 (COGNIS) [oleocetyl alcohol 5 EO];
Mergital OC30 (COGNIS) [oleocetyl alcohol 30 EO];
Brij 72 (UNIQEMA) [stearyl alcohol 2 EO];
Brij 76 (UNIQEMA) [stearyl alcohol 10 EO];
Brij 78P (UNIQEMA) [stearyl alcohol 20 EO];
Brij 700 (UNIQEMA) [stearyl alcohol 100 EO];
Eumulgin B1 (COGNIS) [cetyl stearyl alcohol 12 EO];
Eumulgin L (COGNIS) [cetyl alcohol 9 EO and 2 PO]; and
Witconol APM (GOLDSCHMIDT) [myristyl alcohol 3 PO].

The at least one oxyalkylenated fatty alcohol can be present in an amount ranging from 0.05 to 50% by weight relative to the total weight of the composition, for example from 0.5 to 40% by weight, and for instance from 1 to 20% by weight.

The at least one oxidizing agent present in the composition described herein can be selected from hydrogen peroxide, urea peroxide, alkali bromates, polythionates, and persalts such as perborates, percarbonates and persulfates.

In some embodiments, the at least one oxidizing agent can be hydrogen peroxide.

The at least one oxidizing agent may be present in an amount ranging from 0.1 to 50% by weight relative to the total weight of the composition, for example from 1 to 20% by weight.

In some embodiments, when the at least one oxidizing agent is hydrogen peroxide, the composition described herein may comprise at least one agent that stabilizes hydrogen peroxide.

As examples of agents that stabilize hydrogen peroxide, non-limiting mention may be made of the pyrophosphates of alkali or alkaline-earth metals such as tetrasodium pyrophosphate, the stannates of alkali or alkaline-earth metals, and phenacetin or the salts of acids and oxyquinoline, such as oxyquinoline sulphate. In some embodiments, at least one stannate can be used, optionally combined with at least one pyrophosphate.

The at least one agent that stabilizes hydrogen peroxide may be present in an amount ranging from 0.0001 to 5% by weight relative to the total weight of the composition, and in some embodiments from 0.01 to 2% by weight.

In the composition described herein, the weight ratio of the at least one fatty alcohol to the at least one oxyalkylenated fatty alcohol has a value less than or equal to 5, such as a value ranging from 0.1 to 5, from 0.5 to 4, or from 1 to 3.

The composition may contain at least one oil other than a fatty alcohol described herein. The at least one oil may be present in the composition in an amount greater than or equal to 10% by weight relative to the total weight of the composition, such as greater than or equal to 15% by weight or for example greater than or equal to 20% by weight.

The concentration of oils can range from 10 to 60% by weight relative to the total weight of the composition, for example from 15 to 55% by weight or for instance from 20 to 50% by weight.

"Oil" means, as used herein, a substance that is liquid at 25° C. and at atmospheric pressure (760 mm of mercury), insoluble at those conditions at 5% by weight, and for example at 1% by weight, in water, and has at least one fatty chain containing at least six carbon atoms or at least two siloxane groups.

In some embodiments, the composition may comprise at least one oil which can be selected from mineral, vegetable, animal, or synthetic non-silicone oils and silicone oils.

As non-silicone oils which may be used in the composition described herein, non-limiting mention may be made of, for example:

hydrocarbon oils of animal origin, such as perhydrosqualene;

hydrocarbon oils of vegetable origin, such as liquid triglycerides of fatty acids having from 6 to 30 carbon atoms such as triglycerides of heptanoic or octanoic acids or for example sunflower oil, maize oil, soya oil, cucurbit oil, grapeseed oil, sesame oil, hazelnut oil, apricot oil, macadamia oil, arara oil, sunflower oil, castor oil, avocado oil, triglycerides of caprylic/capric acids such as those sold by the company Stearineries Dubois or those sold under the names MIGLYOL® 810, 812 and 818 by the company Dynamit Nobel, jojoba oil, and shea butter oil;

linear or branched hydrocarbons containing at least 6 carbon atoms, of mineral or synthetic origin, such as $C_6$-$C_{16}$ lower alkanes such as hexane, dodecane, isododecane and isohexadecane, hydrocarbons with more than 16 carbon atoms such as paraffin oils, and the derivatives thereof, vaseline, vaseline oil, polydecenes, and hydrogenated polyisobutene such as PARLÉAM®;

fluorinated, partially hydrocarbon-oils; as fluorinated oils, non-limiting mention may also be made of perfluoromethylcyclopentane and perfluoro-1,3-dimethylcyclohexane, sold under the names "FLUTEC® PC1" and "FLUTEC® PC3" by the Company BNFL Fluorochemicals; perfluoro-1,2-dimethylcyclobutane; perfluoroalkanes such as dodecafluoropentane and tetradecafluorohexane, sold under the names "PF 5050®" and "PF 5060®" by the 3M Company, or bromoperfluorooctyl sold under the name "FORALKYL®" by the company Atochem; nonafluoromethoxybutane and nonafluoroethoxyisobutane; and derivatives of perfluoromorpholine, such as 4-trifluoromethyl perfluoromorpholine sold under the name "PF 5052®" by the 3M Company.

the liquid esters of fatty acids and/or of fatty alcohols other than the triglycerides, and for example those for which the acid and/or the alcohol is/are unsaturated or branched, and for instance isopropyl myristate can be used.

Among the silicone oils that can be used, non-limiting mention may be made of the volatile linear polydialkylsiloxanes with 2 to 9 silicon atoms and having a viscosity less than or equal to $5 \times 10^{-6}$ m$^2$/s at 25° C.; for example, decamethyltetrasiloxane marketed for example under the name "SH 200" by the company TORAY SILICONE. Silicones falling within this class are also described for instance in the article published in Cosmetics and Toiletries, Vol. 91, January 76, p. 27-32-TODD & BYERS "Volatile Silicone fluids for cosmetics".

Non-volatile polydialkylsiloxanes, gums and resins of polydialkylsiloxanes, polyorganosiloxanes modified with the aforementioned organofunctional groups, and mixtures thereof may for example be used.

These silicones may for example be selected from the polydialkylsiloxanes, among which non-limiting mention may be made of polydimethylsiloxanes with trimethylsilyl end groups. The viscosity of the silicones is measured at 25° C. according to standard ASTM 445 Appendix C.

Among these polydialkylsiloxanes, the following non-limiting commercial products may be mentioned:

the SILBIONE® oils of series 47 and 70 047 or the MIRASIL® oils marketed by RHODIA such as, for example, the oil 70 047 V 500000;

the oils of the MIRASIL® series marketed by the company RHODIA;

the oils of the 200 series from the company DOW CORNING such as DC200, with a viscosity of 60000 mm$^2$/s; and the VISCASIL® oils from GENERAL ELECTRIC and certain oils of the SF series (SF 96, SF 18) from GENERAL ELECTRIC.

Mention may also be made of the polydimethylsiloxanes with dimethylsilanol end groups, known under the name dimethiconol (CTFA), such as the oils of the 48 series from the company RHODIA.

In this class of polydialkylsiloxanes, mention may also be made of the products marketed under the names "ABIL WAX® 9800 and 9801" by the company GOLDSCHMIDT, which are polydi($C_1$-$C_{20}$)alkylsiloxanes.

Silicone gums include polydialkylsiloxanes, for example polydimethylsiloxanes having high number-average molecular masses of between 200000 and 1000000, used alone or as a mixture in a solvent. The solvent can be selected from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that can be used for example are mixtures such as:

the mixtures formed from a polydimethylsiloxane hydroxylated at the end of the chain, or dimethiconol (CTFA), and from a cyclic polydimethylsiloxane, also called cyclomethicone (CTFA), such as the product Q2 1401 marketed by the company DOW CORNING;

the mixtures of a polydimethylsiloxane gum and of a cyclic silicone, such as the product SF 1214 Silicone Fluid from the company GENERAL ELECTRIC, which product is a SF 30 gum corresponding to a dimethicone, having a number-average molecular weight of 500000, solubilized in the oil SF 1202 Silicone Fluid corresponding to decamethylcyclopentasiloxane; and the mixtures of two PDMSs of different viscosities, for example of a PDMS gum and of a PDMS oil, such as the product SF 1236 from the company GENERAL ELECTRIC. The product SF 1236 is a mixture of an SE 30 gum defined above, having a viscosity of 20 $m^2$/s, and of an SF 96 oil having a viscosity of $5 \times 10^{-6}$ $m^2$/s. The product preferably comprises 15% of SE 30 gum and 85% of an SF 96 oil.

The organopolysiloxane resins are crosslinked siloxane systems containing the units:

$R_2SiO_{2/2}$, $R_3SiO_{1/2}$, $RSiO_{3/2}$ and $SiO_{4/2}$ in which R represents an alkyl having 1 to 16 carbon atoms. Among the organopolysiloxane resins, mention may be made of those in which R is a $C_1$-$C_4$ lower alkyl group, for instance methyl.

Among these resins, mention may be made of the product marketed under the name "DOW CORNING 593" or those marketed under the names "SILICONE FLUID SS 4230 and SS 4267" by the company GENERAL ELECTRIC and which are silicones of dimethyl/trimethyl siloxane structure.

In some embodiments, the at least one oil other than a fatty alcohol is selected from $C_6$-$C_{16}$ linear and branched alkanes, hydrocarbons containing more than 16 carbon atoms, liquid triglycerides of fatty acids containing from 6 to 30 carbon atoms, fluorinated, partially hydrocarbon-based oils, liquid esters of fatty acids and/or of fatty alcohols other than the triglycerides, and silicone oils.

"Cosmetically acceptable medium" means, as used herein, a medium compatible with keratin fibers, for example human keratin fibers such as the hair.

In some embodiments, the cosmetically acceptable medium of the composition described herein generally comprises water and/or at least one water-soluble organic solvent. As examples of water-soluble organic solvents, non-limiting mention may be made of for example the $C_1$-$C_4$ lower alkanols, such as ethanol and isopropanol; aromatic alcohols such as benzyl alcohol or phenoxyethanol; polyols or polyol ethers such as the monomethyl, monoethyl, and monobutyl ethers of ethylene glycol, propylene glycol or ethers thereof such as monomethyl ether of propylene glycol, butylene glycol, and dipropylene glycol as well as alkyl ethers of diethylene glycol such as monoethyl ether or monobutyl ether of diethylene glycol, or glycerol; and mixtures thereof.

In some embodiments, the at least one water-soluble solvent may be present in an amount ranging from approx. 0.1 to 35% by weight relative to the total weight of the composition described herein, and in some embodiments in an amount ranging from approx. 1 to 40% by weight.

In some embodiments, the composition can also comprise additional compounds used conventionally in cosmetics. These compounds can be selected for example from thickening or stabilizing polymers, non-silicone conditioner polymers, chelating agents, and perfumes.

In some embodiments, the composition described herein may contain at least one $C_8$-$C_{30}$ fatty acid amide, optionally oxyalkylenated. The amide may be present in the composition described herein in an amount ranging from 0.1 to 10% by weight relative to the total weight of the composition, for example from 0.5 to 8% by weight, and for instance from 1 to 5% by weight.

Of course, a person skilled in the art will take care to select this or these optional supplementary compound(s) in such a way that the beneficial properties associated with the composition described herein are not, or substantially are not, affected by the addition or additions envisaged.

The composition can be in various forms, such as in the form of cream, gel, milk, lotion, or mousse, or in any other suitable form for carrying out the treatment of keratin fibers, for example human keratin fibers such as the hair. For example, it can be in the form of a cream or a milk.

In some embodiments, the pH of the oxidizing composition may range from 1.5 to 4.5, for example from 2 to 3.5. It can be adjusted by adding acidifying agents such as hydrochloric acid, acetic acid, lactic acid, boric acid, citric acid, and phosphoric acid or acidifying agents in the presence of alkaline agents.

Also provided herein is a method of treating keratin fibers, comprising applying to the keratin fibers at least one oxidizing composition comprising, a cosmetically acceptable medium;

at least one fatty alcohol;

at least one oxyalkylenated fatty alcohol;

at least one oxidizing agent; and at least one oil other than a fatty alcohol present in an amount greater than or equal to 10% by weight relative to the total weight of the composition;

wherein the weight ratio of the at least one fatty alcohol to the at least one oxyalkylenated fatty alcohol has a value less than or equal to 5; and further wherein the pH of the composition ranges from 1.5 to 4.5.

Also provided herein is a method for treating keratin fibers comprising applying to the keratin fibers at least one oxidizing composition comprising, a cosmetically acceptable medium;

at least one fatty alcohol present in an amount ranging from 3 to 25% by weight relative to the total weight of the composition;

at least one oxyalkylenated fatty alcohol;

at least one oxidizing agent; and at least one oil other than a fatty alcohol present in an amount greater than or equal to 10% by weight relative to the total weight of the composition;

wherein the weight ratio of the at least one fatty alcohol to the at least one oxyalkylenated fatty alcohol has a value less than or equal to 5; and further wherein the pH of the composition is alkaline.

The at least one oxidizing composition described herein can for example be used in a method of dyeing keratin fibers, for example human keratin fibers such as the hair.

The method of dyeing of keratin fibers described herein may employ at least one dyeing composition comprising, in a support suitable for the dyeing of keratin fibers, at least one direct dye and/or at least one oxidation dye and at least one oxidizing composition.

This method comprises applying the at least one dyeing composition to the keratin fibers and developing the color at acidic, neutral, or alkaline pH by means of at least one oxidizing composition, which is applied simultaneously or sequentially, with or without intermediate rinsing.

In some embodiments, the at least one dyeing composition may be mixed, at the moment of use, with at least one oxidizing composition described herein. The mixture obtained may then be applied to the keratin fibers and left in place for a period ranging from 3 to 50 minutes, such as from 5 to 30 minutes, followed by rinsing, washing with shampoo, rinsing again, and drying.

The at least one direct dye can be selected from the direct dyes used conventionally in direct dyeing. As examples, the at least one direct dye may be selected from the nitro dyes of the benzene series, the azo direct dyes, methine direct dyes, quinone direct dyes, azine direct dyes, triarylmethane direct dyes, indoamine direct dyes, and natural direct dyes. These direct dyes can be of nonionic, anionic, or cationic character.

Among the benzene direct dyes, non-limiting mention may be made of 1,4-diamino-2-nitrobenzene, 1-amino-2-nitro-4-(β-hydroxyethylamino)-benzene, 1-amino-2-nitro-4-bis-(β-hydroxyethyl)-aminobenzene, 1,4-bis-(β-hydroxyethylamino)-2-nitrobenzene, 1-β-hydroxyethylamino-2-nitro-4-bis-(β-hydroxyethylamino)-benzene, 1-β-hydroxyethylamino-2-nitro-4-aminobenzene, 1-β-hydroxyethylamino-2-nitro-4-(ethyl)(β-hydroxyethyl)-aminobenzene, 1-amino-3-methyl-4-β-hydroxyethylamino-6-nitrobenzene, 1-amino-2-nitro-4-β-hydroxyethylamino-5-chlorobenzene, 1,2-diamino-4-nitrobenzene, 1-amino-2-β-hydroxyethylamino-5-nitrobenzene, 1,2-bis-(β-hydroxyethylamino)-4-nitrobenzene, 1-amino-2-[tris-(hydroxymethyl)-methylamino]-5-nitrobenzene, 1-hydroxy-2-amino-5-nitrobenzene, 1-hydroxy-2-amino-4-nitrobenzene, 1-hydroxy-3-nitro-4-aminobenzene, 1-hydroxy-2-amino-4,6-dinitrobenzene, 1-β-hydroxyethyloxy-2-β-hydroxyethylamino-5-nitrobenzene, 1-methoxy-2-β-hydroxyethylamino-5-nitrobenzene, 1-β-hydroxyethyloxy-3-methylamino-4-nitrobenzene, 1-β,γ-dihydroxypropyloxy-3-methylamino-4-nitrobenzene, 1-β-hydroxyethylamino-4-β,γ-dihydroxypropyloxy-2-nitrobenzene, 1-β,γ-dihydroxypropylamino-4-trifluoromethyl-2-nitrobenzene, 1-β-hydroxyethylamino-4-trifluoromethyl-2-nitrobenzene, 1-β-hydroxyethylamino-3-methyl-2-nitrobenzene, 1-β-aminoethylamino-5-methoxy-2-nitrobenzene, 1-hydroxy-2-chloro-6-ethylamino-4-nitrobenzene, 1-hydroxy-2-chloro-6-amino-4-nitrobenzene, 1-hydroxy-6-[bis-(β-hydroxyethyl)-amino]-3-nitrobenzene, 1-β-hydroxyethylamino-2-nitrobenzene, and 1-hydroxy-4-β-hydroxyethylamino-3-nitrobenzene.

Among the azo direct dyes, non-limiting mention may be made of the cationic azo dyes described in patent applications WO 95/15144, WO 95/01772, EP 0 714 954, FR 2 822 696, FR 2 825 702, FR 2 825 625, FR 2 822 698, FR 2 822 693, FR 2 822 694, FR 2 829 926, FR 2 807 650, WO 02/078660, WO 02/100834, WO 02/100369 and FR 2 844 269.

Among these dyes, non-limiting mention may be made of for example 1,3-dimethyl-2-[[4-(dimethylamino)phenyl]azo]-1H-imidazolium chloride, 1,3-dimethyl-2-[(4-aminophenyl)azo]-1H-imidazolium chloride, and 1-methyl-4-[(methylphenylhydrazono)methyl]-pyridinium methylsulphate.

Non-limiting mention may also be made of, among the azo direct dyes, the following dyes described in the COLOUR INDEX INTERNATIONAL 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, and Disperse Black 9.

Non-limiting mention may also be made of 1-(4'-aminodiphenylazo)-2-methyl-4-bis-(β-hydroxyethyl)aminobenzene and 4-hydroxy-3-(2-methoxyphenylazo)-1-naphthalene sulphonic acid.

Among the quinone direct dyes, non-limiting mention may be made of the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, and Basic Blue 99, as well as the following dyes: 1-N-methylmorpholiniumpropylamino-4-hydroxyanthraquinone, 1-aminopropylamino-4-methylaminoanthraquinone, 1-aminopropylaminoanthraquinone, 5-β-hydroxyethyl-1,4-diaminoanthraquinone, 2-aminoethylaminoanthraquinone, and 1,4-bis-(β,γ-dihydroxypropylamino)-anthraquinone.

Among the azine dyes, non-limiting mention may be made of the following dyes: Basic Blue 17 and Basic Red 2.

Among the triarylmethane dyes, non-limiting mention may be made of the following dyes: Basic Green 1, Acid Blue 9, Basic Violet 3, Basic Violet 14, Basic Blue 7, Acid Violet 49, Basic Blue 26, and Acid Blue 7.

Among the indoamine dyes, non-limiting mention may be made of the following dyes: 2-β-hydroxyethylamino-5-[bis-(β-4'-hydroxyethyl)amino]anilino-1,4-benzoquinone, 2-β-hydroxyethylamino-5-(2'-methoxy-4'-amino)anilino-1,4-benzoquinone, 3-N(2'-chloro-4'-hydroxy)phenyl-acetylamino-6-methoxy-1,4-benzoquinone imine, 3-N(3'-chloro-4'-methylamino)phenyl-ureido-6-methyl-1,4-benzoquinone imine, and 3-[4'-N-(ethyl, carbamylmethyl)-amino]-phenyl-ureido-6-methyl-1,4-benzoquinone imine.

Among the natural direct dyes that can be used, non-limiting mention may be made of lawsone, juglone, alizarin, purpurin, carminic acid, kermesic acid, purpurogallin, protocatechaldehyde, indigo, isatin, curcumin, spinulosin, apigenidin, and orceins. It is also possible to use extracts or decoctions containing these natural dyes, such as cataplasms or extracts based on henna.

The at least one direct dye may be generally present in the dyeing composition in an amount ranging from 0.001 to 20% by weight relative to the total weight of the composition, for example from 0.005 to 10% by weight.

The at least one oxidation dye can be selected from the oxidation bases and couplers conventionally used in the area of dyeing.

As examples of oxidation bases, non-limiting mention may be made of para-phenylenediamines, double bases, para-aminophenols, ortho-aminophenols, and heterocyclic bases and the addition salts thereof.

Among the para-phenylenediamines, non-limiting mention may be made of, for example, para-phenylenediamine, para-toluenediamine, 2-chloro-para-phenylenediamine, 2,3- dimethyl para-phenylenediamine, 2,6-dimethyl para-phenylenediamine, 2,6-diethyl para-phenylenediamine, 2,5-dimethyl para-phenylenediamine, N,N-dimethyl para-phenylenediamine, N,N-diethyl para-phenylenediamine, N,N-dipropyl para-phenylenediamine, 4-amino N,N-diethyl 3-methyl aniline, N,N-bis-(β-hydroxyethyl) para-phenylenediamine, 4-N,N-bis-(β-hydroxyethyl)amino-2-methyl aniline, 4-N,N-bis-(β-hydroxyethyl)amino-2-chloro aniline, 2-β-hydroxyethyl para-phenylenediamine, 2-fluoro para-phenylenediamine, 2-isopropyl para-phenylenediamine, N-(β-hydroxypropyl) para-phenylenediamine, 2-hydroxymethyl para-phenylenediamine, N,N-dimethyl 3-methyl para-phenylenediamine, N,N-(ethyl, β-hydroxyethyl) para-phenylenediamine, N-(β,γ-dihydroxypropyl) para-phenylenediamine, N-(4'-aminophenyl) para-phenylenediamine, N-phenyl para-phenylenediamine, 2-β-hydroxyethyloxy para-phenylenediamine, 2-β-acetylaminoethyloxy para-phenylenediamine, N-(β-methoxyethyl) para-phenylene-diamine, 4-aminophenylpyrrolidine, 2-thienyl para-phenylenediamine, 2-β hydroxyethylamino-5-aminotoluene, and 3-hydroxy 1-(4'-aminophenyl)pyrrolidine and the addition salts thereof with an acid.

Among the para-phenylenediamines mentioned herein, para-phenylenediamine, para-toluenediamine, 2-isopropyl para-phenylenediamine, 2-β-hydroxyethyl para-phenylenediamine, 2-β-hydroxyethyloxy para-phenylene-diamine, 2,6-dimethyl para-phenylenediamine, 2,6-diethyl para-phenylenediamine, 2,3-dimethyl para-phenylenediamine, N,N-bis-(β-hydroxyethyl) para-phenylenediamine, 2-chloro para-phenylenediamine, and 2-β-acetylaminoethyloxy para-phenylenediamine, and the addition salts thereof with an acid may for example be used.

Among the double bases, non-limiting mention may be made of, as examples, bis-phenylalkylenediamines and bis-para-aminophenols.

Among the bis-phenylalkylenediamines, non-limiting mention may be made of, as examples, N,N'-bis-(β-hydroxyethyl) N,N'-bis-(4'-aminophenyl) 1,3-diamino propanol, N,N'-bis-(β-hydroxyethyl) N,N'-bis-(4'-aminophenyl)ethylenediamine, N,N'-bis-(4-aminophenyl) tetramethylenediamine, N,N'-bis-(β-hydroxyethyl) N,N'-bis-(4-aminophenyl) tetramethylenediamine, N,N'-bis-(4-methyl-aminophenyl) tetramethylenediamine, N,N'-bis-(ethyl) N,N'-bis-(4'-amino, 3'-methylphenyl)ethylenediamine, and 1,8-bis-(2,5-diamino phenoxy)-3,6-dioxaoctane, and the addition salts thereof with an acid.

Among the para-aminophenols, non-limiting mention may be made of, for example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl aminomethyl)phenol, and 4-amino-2-fluorophenol, and the addition salts thereof with an acid.

Among the ortho-aminophenols, non-limiting mention may be made of, for example, 2-aminophenol, 2-amino-5-methylphenol, 2-amino-6-methylphenol, and 5-acetamido-2-aminophenol, and the addition salts thereof with an acid.

Among the heterocyclic bases, non-limiting mention may be made of, for example, pyridine derivatives, pyrimidine derivatives, and pyrazole derivatives.

Among the pyridine derivatives, non-limiting mention may be made of the derivatives described for example in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, and 3,4-diaminopyridine, and the addition salts thereof with an acid.

Other pyridine oxidation bases that can be used are the oxidation bases 3-aminopyrazolo-[1,5-a]-pyridines or the addition salts thereof, described for example in patent application FR 2 801 308. As examples, non-limiting mention may be made of pyrazolo[1,5-a]pyridin-3-ylamine; 2-acetylaminopyrazolo-[1,5-a]pyridin-3-ylamine; 2-morpholin-4-yl-pyrazolo[1,5-a]pyridin-3-ylamine; 3-amino-pyrazolo[1,5-a]pyridine-2-carboxylic acid; 2-methoxy-pyrazolo[1,5-a]pyridin-3-ylamino; (3-amino-pyrazolo[1,5-a]pyridin-7-yl)-methanol; 2-(3-amino-pyrazolo[1,5-a]pyridin-5-yl)-ethanol; 2-(3-amino-pyrazolo[1,5-a]pyridin-7-yl)-ethanol; (3-amino-pyrazolo[1,5-a]pyridin-2-yl)-methanol; 3,6-diamino-pyrazolo[1,5-a]pyridine; 3,4-diamino-pyrazolo[1,5-a]pyridine; pyrazolo[1,5-a]pyridine-3,7-diamine; 7-morpholin-4-yl-pyrazolo[1,5-a]pyridin-3-ylamine; pyrazolo[1,5-a]pyridine-3,5-diamine; 5-morpholin-4-yl-pyrazolo[1,5-a]pyridin-3-ylamine; 2-[(3-amino-pyrazolo[1,5-a]pyridin-5-yl)-(2-hydroxyethyl)-amino]-ethanol; 2-[(3-amino-pyrazolo[1,5-a]pyridin-7-yl)-(2-hydroxyethyl)-amino]-ethanol; 3-amino-pyrazolo[1,5-a]pyridin-5-ol; 3-amino-pyrazolo[1,5-a]pyridin-4-ol; 3-amino-pyrazolo[1,5-a]pyridin-6-ol; and 3-amino-pyrazolo[1,5-a]pyridin-7-ol; as well as the addition salts with an acid or with a base.

Among the pyrimidine derivatives, non-limiting mention may be made of the derivatives described for example in patents DE 2359399; JP 88-169571; JP 05-63124; and EP 0770375 and patent application WO 96/15765 such as 2,4,5,6-tetra-aminopyrimidine, 4-hydroxy 2,5,6-triaminopyrimidine, 2-hydroxy 4,5,6-triaminopyrimidine, 2,4-dihydroxy 5,6-diaminopyrimidine, and 2,5,6-triaminopyrimidine; and pyrazolo-pyrimidine derivatives such as those mentioned in patent application FR-A-2750048 and among which non-limiting mention may be made of pyrazolo-[1,5-a]-pyrimidine-3,7-diamine; 2,5-dimethyl pyrazolo-[1,5-a]-pyrimidine-3,7-diamine; pyrazolo-[1,5-a]-pyrimidine-3,5-diamine; 2,7-dimethylpyrazolo-[1,5-a]-pyrimidine-3,5-diamine; 3-aminopyrazolo-[1,5-a]-pyrimidin-7-ol; 3-aminopyrazolo-[1,5-a]-pyrimidin-5-ol; 2-(3-aminopyrazolo-[1,5-a]-pyrimidin-7-ylamino)-ethanol, 2-(7-aminopyrazolo-[1,5-a]-pyrimidin-3-ylamino)-ethanol, 2-[(3-amino-pyrazolo[1,5-a]pyrimidin-7-yl)-(2-hydroxy-ethyl)-amino]-ethanol, 2-[(7-amino-pyrazolo[1,5-a]pyrimidin-3-yl)-(2-hydroxy-ethyl)-amino]-ethanol, 5,6-dimethylpyrazolo-[1,5-a]-pyrimidine-3,7-diamine, 2,6-dimethylpyrazolo-[1,5-a]-pyrimidine-3,7-diamine, 2,5,N7,N7-tetramethyl pyrazolo-[1,5-a]-pyrimidine-3,7-diamine, and 3-amino-5-methyl-7-imidazolylpropylaminopyrazolo-[1,5-a]-pyrimidine and the addition salts thereof with an acid and the tautomeric forms thereof, when there is tautomeric equilibrium.

Among the pyrazole derivatives, non-limiting mention may be made of the derivatives described in patents DE 3843892 and DE 4133957 and patent applications WO 94/08969, WO 94/08970, FR-A-2 733 749 and DE 195 43 988 such as 4,5-diamino 1-methylpyrazole, 4,5-diamino 1-(β-hydroxyethyl)pyrazole, 3,4-diaminopyrazole, 4,5-diamino 1-(4'-chlorobenzyl)pyrazole, 4,5-diamino 1,3-dimethylpyrazole, 4,5-diamino-3-methyl 1-phenyl pyrazole, 4,5-diamino 1-methyl 3-phenyl pyrazole, 4-amino 1,3-dimethyl 5-hydrazino pyrazole, 1-benzyl 4,5-diamino-3-methylpyrazole, 4,5-diamino-3-tert-butyl 1-methylpyrazole, 4,5-diamino 1-tert-butyl 3-methylpyrazole, 4,5-diamino 1-(β-hydroxyethyl) 3-methylpyrazole, 4,5-diamino 1-ethyl 3-methylpyrazole, 4,5-diamino 1-ethyl 3-(4'-methoxyphenyl)pyrazole, 4,5-diamino 1-ethyl 3-hydroxymethylpyrazole, 4,5-diamino-3-hydroxymethyl 1-methylpyrazole, 4,5- diamino-3-hydroxymethyl 1-isopropyl pyrazole, 4,5-diamino-3-methyl 1-isopropyl pyrazole, 4-amino-5-(2'-aminoethyl)amino 1,3-dimethyl pyrazole, 3,4,5-triaminopyrazole, 1-methyl 3,4,5-triaminopyrazole, 3,5-diamino 1-methyl 4-methylaminopyrazole, and 3,5-diamino 4-(β-hydroxyethyl)amino 1-methylpyrazole, and the addition salts thereof with an acid.

As pyrazole derivatives, non-limiting mention may be made of the diamino-N,N-dihydropyrazopyrazolones and for example those described in application FR 2 886 136 such as the following derivatives and the addition salts thereof.

Among these derivatives, non-limiting mention may be made of the following:
2,3-diamino-6,7-dihydro-1H,5H-pyrazolo[1,2-a]pyrazol-1-one,
2-amino-3-ethylamino-6,7-dihydro-1H,5H-pyrazolo[1,2-a]pyrazol-1-one,
2-amino-3-isopropylamino-6,7-dihydro-1H,5H-pyrazolo[1,2-a]pyrazol-1-one,
2-amino-3-(pyrrolidin-1-yl)-6,7-dihydro-1H,5H-pyrazolo[1,2-a]pyrazol-1-one,
4,5-diamino-1,2-dimethyl-1,2-dihydro-pyrazol-3-one,
4,5-diamino-1,2-diethyl-1,2-dihydro-pyrazol-3-one,
4,5-diamino-1,2-di-(2-hydroxyethyl)-1,2-dihydro-pyrazol-3-one,
2-amino-3-(2-hydroxyethyl)amino-6,7-dihydro-1H,5H-pyrazolo[1,2-a]pyrazol-1-one,
2-amino-3-dimethylamino-6,7-dihydro-1H,5H-pyrazolo[1,2-a]pyrazol-1-one,
2,3-diamino-5,6,7,8-tetrahydro-1H,6H-pyridazino[1,2-a]pyrazol-1-one,
4-amino-1,2-diethyl-5-(pyrrolidin-1-yl)-1,2-dihydro-pyrazol-3-one,
4-amino-5-(3-dimethylamino-pyrrolidin-1-yl)-1,2-diethyl-1,2-dihydro-pyrazol-3-one, and
2,3-diamino-6-hydroxy-6,7-dihydro-1H,5H-pyrazolo[1,2-a]pyrazol-1-one.

For example, 4,5-diamino 1-β-hydroxyethyl)pyrazole and 2,3-diamino-6,7-dihydro-1H,5H-pyrazolo[1,2-a]pyrazol-1-one and the addition salts thereof may be used as heterocyclic bases.

In some embodiments, the at least one oxidation base may generally be present in the dyeing composition in an amount ranging from 0.001 to 10% by weight relative to the total weight of the composition, such as from 0.005 to 6% by weight.

As examples of couplers, non-limiting mention may be made of meta-phenylenediamines, meta-aminophenols, meta-diphenols, naphthalenic couplers, and heterocyclic couplers and the addition salts thereof.

Non-limiting mention may also be made of 2-methyl 5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy 2-methyl benzene, 4-chloro 1,3-dihydroxybenzene, 2,4-diamino 1-(β-hydroxyethyloxy)benzene, 2-amino 4-(β-hydroxyethylamino) 1-methoxybenzene, 1,3-diamino benzene, 1,3-bis-(2,4-diaminophenoxy) propane, 3-ureido aniline, 3-ureido 1-dimethylamino benzene, sesamol, 1-β-hydroxyethylamino-3,4-methylenedioxybenzene, α-naphthol, 2-methyl-1-naphthol, 6-hydroxy indole, 4-hydroxy indole, 4-hydroxy N-methyl indole, 2-amino-3-hydroxypyridine, 6-hydroxy benzomorpholine 3,5-diamino-2,6-dimethoxypyridine, 1-N-(β-hydroxyethyl)amino-3,4-methylene dioxybenzene, and 2,6-bis-(β-hydroxyethylamino)toluene and the addition salts thereof with an acid.

In some embodiments, the at least one coupler may generally be present in the dyeing composition in an amount ranging from 0.001 to 10% by weight relative to the total weight of the composition, such as from 0.005 to 6% by weight.

In general, the addition salts of the at least one oxidation base and of the at least one coupler that can be used are for example selected from the addition salts thereof with an acid, such as hydrochlorides, hydrobromides, sulphates, citrates, succinates, tartrates, lactates, tosylates, benzenesulphonates, phosphates, and acetates and addition salts thereof with a base such as sodium hydroxide, potassium hydroxide, ammonia, amines, and alkanolamines.

The at least one oxidizing composition can also be used in a method of bleaching keratin fibers, for example human keratin fibers such as the hair.

In some embodiments, the method of bleaching comprises applying to the keratin fibers a bleaching composition for example comprising hydrogen peroxide in an alkaline medium after extemporaneous mixing. In some embodiments, the method of bleaching also comprises rinsing the keratin fibers.

In some embodiments, the bleaching composition applied to the keratin fibers can be obtained by mixing at least one oxidizing composition with an aqueous or anhydrous composition for example containing at least one alkaline agent. The at least one alkaline agent can be selected from aqueous ammonia, alkanolamines, including monoethanolamine, amino acids for example basic amino acids such as lysine or arginine, alkali-metal carbonates or bicarbonates, alkali-metal hydroxides, and guanidine carbonate and mixtures thereof. The anhydrous composition can be pulverulent or in the form of paste and, in both cases, may for example contain at least one peroxidized salt, such as at least one persulphate. The anhydrous composition in the form of paste may additionally contain at least one inert organic liquid.

Also provided herein is a method for permanently deforming keratin fibers, for example human keratin fibers such as the hair, using at least one oxidizing composition described herein.

This method compromises applying at least one reducing composition to the keratin fibers to be treated, placing the keratin fibers under mechanical tension before, during, or after application of the at least one reducing composition, optionally rinsing the fibers, applying the at least one oxidizing composition described herein to the optionally rinsed fibers, and then optionally rinsing the fibers again.

This method comprises applying at least one reducing composition to the hair. Application may be carried out lock by lock or globally.

The at least one reducing composition comprises at least one reducing agent, which may be selected for example from thioglycolic acid, cysteine, cysteamine, glycerol thioglycolate, thiolactic acid, and the salts thereof of thiolactic and thioglycolic acids.

The hair may be placed under tension in a form corresponding to the desired final form for the hair (curls for example) via any device or method, for example mechanical, that is appropriate and is known per se for keeping the hair under tension, for example rollers, curlers, combs and the like.

The hair can also be shaped without using external aids, such as with the fingers.

Before optionally rinsing, the hair on which the at least one reducing composition has been applied should, conventionally, be left for some minutes, generally for a period of time ranging from 5 minutes to one hour, such as from 10 to 30 minutes, to give the at least one reducing agent time to act on the hair. This waiting period may for example be carried out at a temperature ranging from 35° C. to 45° C., for instance while also protecting the hair with a cap.

The optional rinsing may be accomplished by carefully rinsing the hair impregnated with the at least one reducing composition with an aqueous composition.

Then, the at least one oxidizing composition described herein may be applied to the hair thus rinsed to fix the new shape imposed on the hair.

As in the case of application of the at least one reducing composition, the hair to which the at least one oxidizing composition has been applied may then, conventionally, be left alone for a resting or waiting period, which may last for a period of some minutes, for example ranging from 3 to 30 minutes, such as from 5 to 15 minutes.

If the tension of the hair has been maintained by external means, the latter (rollers, curlers and the like) can be removed from the hair before or after fixation.

Finally, the hair impregnated with the at least one oxidizing composition may optionally be rinsed carefully, generally with water.

Also provided herein is the use of at least one oxidizing composition described herein for treating keratin fibers, for example human keratin fibers such as the hair.

Also provided herein is the use of at least one oxidizing composition described herein for dyeing keratin fibers, for example human keratin fibers such as the hair.

Also provided herein is the use of at least one oxidizing composition described herein for bleaching keratin fibers, for example human keratin fibers such as the hair.

Also provided herein is the use of at least one oxidizing composition described herein for permanently deforming keratin fibers, for example human keratin fibers such as the hair.

The following examples illustrate the disclosure but are not in any way limiting.

EXAMPLES

The following compositions were prepared:

| Composition | A | B |
|---|---|---|
| Diethylenetriamine pentaacetic acid, pentasodium salt in 40% aqueous solution | 0.15 g | 0.15 g |
| Hydrogen peroxide in solution at 50% (hydrogen peroxide 200 volumes) | 12 g | 12 g |
| Sodium stannate | 0.04 g | 0.04 g |
| Tetrasodium pyrophosphate, 10 H$_2$O | 0.03 g | 0.03 g |
| Tetramethyl hexamethylenediamine/dichloro-1,3-propylene polycondensate in aqueous solution sold under the name MEXOMERE PO by the company Chimex | 0.25 g | 0.25 g |
| Poly-dimethyl-diallyl ammonium chloride in water at 40%, unstabilized, sold under the name MERQUAT 100 by the company Nalco | 0.50 g | 0.50 g |
| Deionized water | 49.13 g | 50.73 g |
| Vaseline oil | 25 g | 25 g |
| Glycerol | 0.50 g | 0.50 g |
| Stearyl alcohol 30/70 | 8 g | 8 g |
| Ceteareth-33 | 3 g | 1.40 g |
| Ethoxylated amide of colza acids (4 EO) protected | 1.30 g | 1.30 g |
| Vitamin E | 0.10 g | 0.10 g |
| Phosphoric acid q.s. | pH 2 | pH 2 |

Composition B was not stable, with phase separation occurring 15 days after the formulation, at 45° C. In composition B, the weight ratio of the at least one fatty alcohol to the at least one oxyalkylenated fatty alcohol had a value equal to 5.7.

Composition A was stable, even after two months stored at 45° C. In composition A, the weight ratio of the at least one fatty alcohol to the at least one oxyalkylenated fatty alcohol had a value equal to 2.7.

What is claimed is:

1. A composition for the treatment of keratin fibers comprising,
    a cosmetically acceptable medium;
    at least one fatty alcohol selected from non-(poly)oxyalkylenated and non-(poly)glycerolated saturated monoalcohols containing from 14 to 22 carbon atoms;
    at least one oxyalkylenated fatty alcohol selected from linear or branched, saturated or unsaturated oxyalkylenated fatty alcohols containing from 8 to 40 carbon atoms and from 1 to 250 ethylene oxide and/or propylene oxide groups;
    at least one oxidizing agent;
    at least one oxyalkylenated $C_8$-$C_{30}$ fatty acid amide, present in an amount ranging from 0.1% to 10%; and
    at least one oil other than a fatty alcohol present in an amount greater than or equal to 10% by weight relative to the total weight of the composition;
    wherein the weight ratio of the at least one fatty alcohol to the at least one oxyalkylenated fatty alcohol has a value less than or equal to 5; and
    further wherein the pH of the composition ranges from 1.5 to 4.5.

2. A composition for the treatment of keratin fibers comprising
    a cosmetically acceptable medium;
    at least one fatty alcohol selected from non-(poly)oxyalkylenated and non-(poly)glycerolated saturated monoalcohols containing from 14 to 22 carbon atoms, present in an amount ranging from 3 to 25% by weight relative to the total weight of the composition;
    at least one oxyalkylenated fatty alcohol selected from linear or branched, saturated or unsaturated oxyalkylenated fatty alcohols containing from 8 to 40 carbon atoms and from 1 to 250 ethylene oxide and/or propylene oxide groups;
    at least one oxidizing agent;
    at least one oxyalkylenated $C_8$-$C_{30}$ fatty acid amide, present in an amount ranging from 0.1% to 10%; and
    at least one oil other than a fatty alcohol present in an amount greater than or equal to 10% by weight relative to the total weight of the composition;
    wherein the weight ratio of the at least one fatty alcohol to the at least one oxyalkylenated fatty alcohol has a value less than or equal to 5; and
    further wherein the pH of the composition is alkaline.

3. A composition according to claim 1, wherein the at least one fatty alcohol is present in an amount ranging from 3 to 25% by weight relative to the total weight of the composition.

4. A composition according to claim 1, wherein the at least one oxyalkylenated fatty alcohol contains from 10 to 20 carbon atoms and from 2 to 40 ethylene oxide groups.

5. A composition according to claim 1, wherein the at least one oxyalkylenated fatty alcohol is present in an amount ranging from 0.05 to 50% by weight relative to the total weight of the composition.

6. A composition according to claim 1, wherein the at least one oxidizing agent is selected from hydrogen peroxide, urea peroxide, alkaline bromates, polythionates and persalts.

7. A composition according to claim 1, wherein the at least one oxidizing agent is present in an amount ranging from 0.1 to 50% by weight relative to the total weight of the composition.

8. A composition according to claim 1, wherein the weight ratio of the at least one fatty alcohol to the at least one oxyalkylenated fatty alcohol has a value ranging from 0.1 to 5.

9. A composition according to claim 1, wherein the at least one oil other than a fatty alcohol is present in an amount greater than or equal to 15% by weight, relative to the total weight of the composition.

10. A composition according to claim 1, wherein the at least one oil other than a fatty alcohol is selected from $C_6$-$C_{16}$ linear and branched alkanes; hydrocarbons containing more than 16 carbon atoms; liquid triglycerides of fatty acids containing from 6 to 30 carbon atoms; fluorinated, partially hydrocarbon-based oils; liquid esters of fatty acids and/or of fatty alcohols other than the triglycerides and silicone oils.

11. A method for treating keratin fibers, comprising applying to the keratin fibers at least one oxidizing composition comprising,
a cosmetically acceptable medium;
at least one fatty alcohol selected from non-(poly)oxyalkylenated and non-(poly)glycerolated saturated monoalcohols containing from 14 to 22 carbon atoms;
at least one oxyalkylenated fatty alcohol selected from linear or branched, saturated or unsaturated oxyalkylenated fatty alcohols containing from 8 to 40 carbon atoms and from 1 to 250 ethylene oxide and/or propylene oxide groups;
at least one oxidizing agent;
at least one oxyalkylenated $C_8$-$C_{30}$ fatty acid amide, present in an amount ranging from 0.1% to 10%; and
at least one oil other than a fatty alcohol present in an amount greater than or equal to 10% by weight relative to the total weight of the composition;
wherein the weight ratio of the at least one fatty alcohol to the at least one oxyalkylenated fatty alcohol has a value less than or equal to 5; and
further wherein the pH of the composition ranges from 1.5 to 4.5.

12. A method for treating keratin fibers, comprising applying to the keratin fibers at least one oxidizing composition comprising,
a cosmetically acceptable medium;
at least one fatty alcohol selected from non-(poly)oxyalkylenated and non-(poly)glycerolated saturated monoalcohols containing from 14 to 22 carbon atoms, present in an amount ranging from 3 to 25% by weight relative to the total weight of the composition;
at least one oxyalkylenated fatty alcohol selected from linear or branched, saturated or unsaturated oxyalkylenated fatty alcohols containing from 8 to 40 carbon atoms and from 1 to 250 ethylene oxide and/or propylene oxide groups;
at least one oxidizing agent;
at least one oxyalkylenated $C_8$-$C_{30}$ fatty acid amide, present in an amount ranging from 0.1% to 10%; and
at least one oil other than a fatty alcohol present in an amount greater than or equal to 10% by weight relative to the total weight of the composition;
wherein the weight ratio of the at least one fatty alcohol to the at least one oxyalkylenated fatty alcohol has a value less than or equal to 5; and
further wherein the pH of the composition is alkaline.

13. A method for making an oxidizing composition for treating keratin fibers comprising combining,
a cosmetically acceptable medium;
at least one fatty alcohol selected from non-(poly)oxyalkylenated and non-(poly)glycerolated saturated monoalcohols containing from 14 to 22 carbon atoms;
at least one oxyalkylenated fatty alcohol selected from linear or branched, saturated or unsaturated oxyalkylenated fatty alcohols containing from 8 to 40 carbon atoms and from 1 to 250 ethylene oxide and/or propylene oxide groups;
at least one oxidizing agent;
at least one oxyalkylenated $C_8$-$C_{30}$ fatty acid amide, present in an amount ranging from 0.1% to 10%; and
at least one oil other than a fatty alcohol present in an amount greater than or equal to 10% by weight relative to the total weight of the composition;
wherein the weight ratio of the at least one fatty alcohol to the at least one oxyalkylenated fatty alcohol has a value less than or equal to 5;
further wherein the pH of the composition ranges from 1.5 to 4.5; and
wherein the ingredients can be added in any order.

14. A method for making an oxidizing composition for treating keratin fibers, comprising combining,
a cosmetically acceptable medium;
at least one fatty alcohol selected from non-(poly)oxyalkylenated and non-(poly)glycerolated saturated monoalcohols containing from 14 to 22 carbon atoms, present in an amount ranging from 3 to 25% by weight relative to the total weight of the composition;
at least one oxyalkylenated fatty alcohol selected from linear or branched, saturated or unsaturated oxyalkylenated fatty alcohols containing from 8 to 40 carbon atoms and from 1 to 250 ethylene oxide and/or propylene oxide groups;
at least one oxidizing agent;
at least one oxyalkylenated $C_8$-$C_{30}$ fatty acid amide, present in an amount ranging from 0.1% to 10%; and
at least one oil other than a fatty alcohol present in an amount greater than or equal to 10% by weight relative to the total weight of the composition;
wherein the weight ratio of the at least one fatty alcohol to the at least one oxyalkylenated fatty alcohol has a value less than or equal to 5;
further wherein the pH of the composition is alkaline; and
wherein the ingredients can be added in any order.

* * * * *